(12) United States Patent
Ooi et al.

(10) Patent No.: US 10,731,124 B2
(45) Date of Patent: Aug. 4, 2020

(54) DEVICE FOR DISRUPTING TISSUE

(71) Applicant: Celligenics Pte. Ltd., Singapore (SG)

(72) Inventors: Zi Yang Ooi, Singapore (SG); Pamela Mok, Singapore (SG); Aimin Yeo, Singapore (SG)

(73) Assignee: Celligenics Pte. Ltd., Singapore (SG)

( * ) Notice: Subject to any disclaimer, the term of this patent is extended or adjusted under 35 U.S.C. 154(b) by 0 days.

(21) Appl. No.: 16/337,527

(22) PCT Filed: Oct. 23, 2017

(86) PCT No.: PCT/SG2017/050529
§ 371 (c)(1),
(2) Date: Mar. 28, 2019

(87) PCT Pub. No.: WO2018/088959
PCT Pub. Date: May 17, 2018

(65) Prior Publication Data
US 2019/0225929 A1    Jul. 25, 2019

(30) Foreign Application Priority Data

Nov. 10, 2016   (GB) .................................. 1618972.2

(51) Int. Cl.
*C12M 1/33*  (2006.01)
*G01N 1/28*  (2006.01)

(52) U.S. Cl.
CPC .............. *C12M 45/02* (2013.01); *G01N 1/286* (2013.01); *G01N 2001/2866* (2013.01)

(58) Field of Classification Search
None
See application file for complete search history.

(56) References Cited

U.S. PATENT DOCUMENTS 6,398,402 B1   6/2002  Thomas et al.
2004/0097829 A1  5/2004  McRury et al.

FOREIGN PATENT DOCUMENTS

| JP | 2012/024061 A | 2/2012 | |
| WO | WO 2015/117007 A1 | 8/2015 | |
| WO | WO 2016/095390 A1 | 6/2016 | |
| WO | WO-2016095390 A1 * | 6/2016 | ............... G01N 1/28 |
| WO | WO 2016/134132 A1 | 8/2016 | |

OTHER PUBLICATIONS

PCT/SG2017/050529 Written Opinion and International Search Report dated Jan. 4, 2018 (10 pages).
PCT/SG2017/050529 International Preliminary Examination Report dated Jun. 12, 2018 (12 pages).
Search Report issued in Great Britain Application No. 1618972.2, dated Sep. 19, 2017 (5 Pages).

* cited by examiner

*Primary Examiner* — Matthew D Krcha
(74) *Attorney, Agent, or Firm* — Klarquist Sparkman, LLP

(57) ABSTRACT

The invention relates to a device that is adapted for disrupting tissue using mechanical separation; and the use of said device for said purpose.

24 Claims, 5 Drawing Sheets

DEVICE FOR DISRUPTING TISSUE

CROSS REFERENCE TO RELATED APPLICATIONS

This is the U.S. National Stage of International Application No. PCT/SG2017/050529, filed Oct. 23, 2017, which was published in English under PCT Article 21(2), which in turn claims the benefit of Great Britain Application No. 1618972.2, filed Nov. 10, 2016.

FIELD OF THE INVENTION

The invention relates to a device that is adapted for the disruption of tissue from a sample using mechanical extraction; and the use of said device for said purpose.

BACKGROUND OF THE INVENTION

Many cell therapies available for use today involve the use of specific tissue types, such as stem cells. These cells are used in a number of technologies but are particularly important in personalised or regenerative medicine. The use of these cells typically necessitates their isolation from a larger sample or organ, or part of an organ. Whilst, traditionally, tissue has been isolated using enzymatic digestion this can be slow, aggressive and indiscriminative. For example, it is known to use collagenase or other dissociating enzymes to breakdown the extracellular matrix, followed by centrifugation to separate the components of the extract. However calibrating the amount of collagenase so that just enough is used to disrupt the extracellular matrix whilst leaving the target tissue intact and fully functional is more of an art than a science and is influenced by the age of the tissue to be treated as well as its structural components and the relative amounts of those components. Moreover the task is further compounded by the fact that the activity of dissociating enzymes degrades over time and even from batch to batch and so each time an enzymatic digestion is performed a careful pre-calibration of the active enzyme needs to be undertaken. With all these variables, it is not surprising that the digestion results are often variable.

Cells can be isolated from a number of tissue types, for example Islets of Langerhans can be isolated form the pancreas, myocytes from the heart and stem cells from the bone marrow, oral mucosa and adipose tissue—to name just a few. However, it is necessary to ensure the isolated cell types retain their inherent functionality which, in the case of stem cells, is the ability to proliferate and give rise to multiple tissue types such as bone, cartilage, muscle, nerve, endocrine, epithelia and endothelia. Additionally, a source of stem cells or progenitor cells are also used for creating induced pluripotent stem cells.

It follows that if the isolation of cells is to be successful they must give rise to functional extracts and so a method of isolation that safeguards against cell damage is favoured. To this end, we report herein a form of mechanical extraction that favours the isolation of functional cell types and in particular stem or progenitor cells.

STATEMENTS OF INVENTION

According to a first aspect of the invention there is therefore provided a device for use in disrupting tissue wherein said device comprises a first moving part in the form of an elongate shaft having attached thereto or associated therewith at least one continuous or discontinuous helical ribbon/screw thread and a second non-moving part in the form of a casing adapted to fit over said shaft and having at least one elongate aperture aligned with the longitudinal axis of said shaft and being wider at an end remote from a tissue contact end.

In a preferred embodiment of the invention said moving part comprises a motor, ideally comprising a rotor. More preferably said moving part comprises a handle or mounting via which it can be held whilst in operation.

Yet more preferably, more than one of said ribbons/threads is provided; a first and a second and they originate from opposite parts of said casing, usually they are spaced 180° apart having regard to the diameter of said casing and they run in the same direction along the lower part of said shaft, although in some embodiments the two ribbons/threads may originate from different locations on said shaft and indeed terminate at different locations.

The component parts referred to herein as helical ribbons are connected to the central shaft by means of regularly spaced rods, for example we currently have one connecting rod every 90° turn of the thread, though other spacings may be preferred for some configurations. The component parts referred to herein as screw threads are typically fashioned or gouged into the structure of the shaft.

In yet a further embodiment a third ribbon/screw thread is provided on the upper part of said shaft and its direction of rotation is the opposite to that of the other first and/or second ribbon(s)/screw threads. Thus, ideally, with respect to the use of said device, a lower part or half of said shaft is provided with at least one first screw ribbon/thread and in some embodiments a second screw ribbon/thread, and in the instance where a third screw ribbon/thread is provided, it is attached to or formed on the upper part or half of said shaft.

In our preferred arrangement we thus have 3 helical ribbons or screw threads: two lower ones running in the same direction, but originating 180° apart, and one above, running in the opposite direction.

More ideally still said ribbon(s) or thread(s) are continuous, thus a first or second ribbon/thread rotates continuously or uninterruptedly in a first direction and a third ribbon/thread rotates continuously or uninterruptedly in a second direction.

Yet more preferred, the angular arrangement of the screw ribbon(s)/thread(s) ranges from 20°-88° as measured from a horizontal plane. The preferred angular arrangement is within a range of 40°-80°, yet more preferably the angular arrangement is within a range of 50°-60°.

Yet more advantageously, the depth of the ribbons(s)/screw thread(s) is less than 40% of the diameter of the casing and more preferably less than 30% of the diameter of the casing.

Yet more preferably still said casing comprises a plurality of apertures. Typically, but not exclusively, between 2-12 per casing circumference, more ideally still, 4 apertures per approximate 4 cm of casing, although those skilled in the art will appreciate the number of apertures can vary according to requirements, furthermore, ideally, said apertures are evenly spaced about said casing.

In a preferred embodiment said, or each, aperture comprises a slit whose size expands at an end remote from said tissue contact end, ideally, to form a partial circular shape.

However in other embodiments, said aperture comprises a discontinuous slit whose size expands at said end remote from said tissue contact end.

Preferably the expanded part of said aperture(s) is aligned with the upper end of said first and/or second thread, or is aligned with a junction between said first and third threads.

More preferably still said motor and/or rotor is provided within the casing.

In particularly preferred embodiments, the lower or tissue contact region of the elongate shaft is free of any attached or associated screw thread(s), and an engaging member, typically a bracket, is provided either on said shaft or said casing whereby the elongate shaft is free to rotate but is relatively laterally restrained by said bracket, thereby maintaining alignment of the first moving part with respect to the second non-moving part of the device during the tissue dissociation process. Most ideally, the lower or tissue contact end of the casing comprises a bracket with an aperture that is aligned with, or concentric with, the longitudinal axis of the elongate shaft and is configured to accommodate the terminal region of the elongate shaft. In this embodiment reproducibility of the tissue dissociation process and the performance of the device is improved. In an alternative embodiment, said lower or tissue contact region of the elongate shaft is free of any attached or associated screw thread(s) and a bracket or skirt member is provided on same of a size and shape so that clearance is provided between it and the casing whereby the elongate shaft is free to rotate but is relatively laterally restrained by the clearance provided between said bracket or skirt member and said casing.

In use, the device is held steady manually or via use of a conventional mounting and the rotor is activated whereby the shaft rotates thus, via its thread or threads, creating an agitator that disrupts tissue connections. Further the use of an apertured outer casing ensures disrupted tissue that travels, or rises, along said first and/or ribbon/thread is ejected from said device via said one or more apertures and ideally at the expanded end thereof. The use of a third, optional, upper ribbon/thread rotating in an opposite direction, with respect to said first and/or second ribbon/thread and terminating at or near said expanded part of said aperture ensures disrupted tissue does not travel along the entire length of said shaft but rather is directed to exit where the two oppositely wound first/third threads meet which is typically aligned with the expanded part of said aperture.

According to a second aspect of the invention there is provided a method for disrupting tissue comprising the use of the afore device and a selected tissue sample whose component parts are to be mechanically separated.

In a preferred method said tissue is suspended in a biocompatible fluid (e.g. normal saline, Hank's balanced salt solutions with or without calcium and magnesium, phosphate buffered salt solution with or without calcium and magnesium, Ringer's solution, lactated Ringer's solution, Hartmann's solution), with or without additives that are biocompatible/clinically approved excipients/reagents including, but not limited to, polyethylene glycol, polyvinyl alcohol, sucrose, albumin, amino acid, pyruvate, alone or in combination, for increasing the number of live, intact cells obtained.

In a preferred method the rotation speed(s) of said device ranges from 100-10,000 revolutions per minute. Moreover, the duration(s) of rotation(s) ranges from 10 seconds-10 minutes.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF SUMMARY OF THE DRAWINGS

An embodiment of the invention will now be described by way of example only with reference to the following figures where.

Figure 1:
FIG. 1 shows a side view of a first moving part in accordance with the invention.
Figure 2:
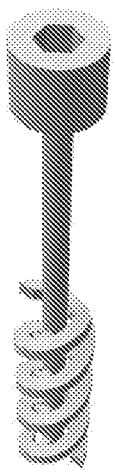
FIG. 2 shows a slanted side view of a first moving part in accordance with the invention.
Figure 3:
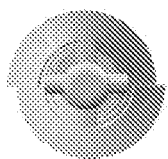
FIG. 3 shows a bottom view of a first moving part in accordance with the invention having a first and second screw thread.

Referring firstly to FIG. 1, an exploded view of the device is shown wherein the inner moving part has been removed from its outer casing. Attached to, or integral with, the central shaft there is provided at least one first helical ribbon which winds its way along a part of said shaft, ideally, it winds its way along a lower part that constitutes approximately half the length of said shaft. The thread is either connected to said shaft using cross-struts/rods or made integral therewith during manufacture. The struts are regularly spaced, for example we currently have one connecting strut/rod every 90° turn of the ribbon. The angular arrangement of the helix ranges from 20°-88°, ideally 40°-80° or 50°-60°, as measured from a horizontal plane. The channel depth of the helical ribbon is less than 40%, ideally less than 30°, of the diameter of an outer static casing, described below. In certain embodiments a second lower helical ribbon is provided and it is ideally spaced 180° apart from said first helical ribbon i.e. it originates on opposite side of said casing having regard to said first helical ribbon but it runs in the same direction.

The component parts referred herein as helical ribbon may take the form of a screw thread that is formed in the central shaft.

Figure 4:
FIG. 4 shows a side view of a first moving part in accordance with a preferred embodiment of the invention having a first, second and third screw thread, wherein the direction of rotation of the first (lower) and second (lower) screw threads are opposite to the direction of rotation of the third screw thread.

In FIG. 4 there is shown an optional feature which comprises a third helical ribbon also either attached to, or integral with, the central shaft. It, too, winds its way along a part of said shaft, ideally, it winds its way along an upper part that constitutes approximately half the length of said shaft. This helical ribbon is also either connected to said shaft using cross-struts/rods or made integral therewith during manufacture. The direction of turn of the third or upper helical ribbon is opposite to that of the first or lower helical ribbon. Moreover, the periodicity of the third or upper helical ribbon tends to be less than that of the lower helical ribbon(s). This is because the lower helical ribbon(s) performs largely a disruptive function whereas the upper helical ribbon performs a directional function ensuring dissociated tissue exits said device at the appropriate place.

In our preferred arrangement we thus have 3 helical ribbons or screw threads: two lower ones running in the same direction, but originating 180° apart, and one above, running in an opposite direction.

Figure 5:
FIG. 5 shows a slanted side view of the first moving part shown in FIG. 4.

Whilst in FIG. 5 the two ribbons are shown as connected or continuous (their periodicity determining their delineation) the two ribbons may be unconnected or discontinuous.

Figure 6:
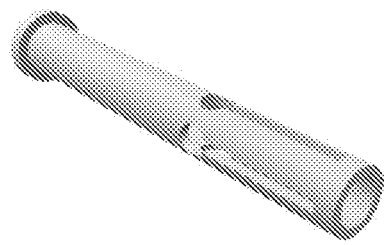
FIG. 6 shows a slanted side view of a second non-moving part or casing according to one embodiment of the invention.
Figure 7:
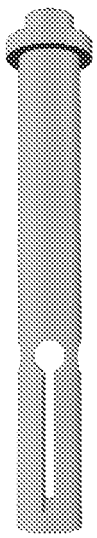
FIG. 7 shows an upright side view of the casing shown in FIG. 6.
Figure 8:
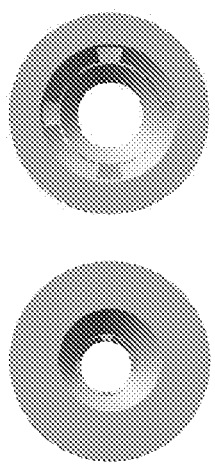
FIG. 8 shows a bottom and top view of the casing shown in FIGS. 6 and 7.

In FIG. 6 there is shown an outer casing, this an exploded view of the device where the outer non-moving part has been removed from the inner shaft.

The casing comprises a hollow cylinder which is sized and shaped to fit about the moving part. At its lower end, the end that fits over the first/second lower screw thread(s) it comprises at least one and, typically, a plurality of opening or slits which may be spaced from the lower edge of the casing or contiguous therewith. In the embodiment shown the apertures are spaced form the lower end of the casing. The apertures are slits aligned with the longitudinal axis of the casing or the shaft over which the casing fits and, usually, evenly distributed about the circumferential axis of the casing. Typically, the number of holes range from 2-12 per casing circumference and in the embodiment shown 4 per 4 cm of casing circumference.

Although not shown, a rotor is placed within the casing and operatively coupled to the moving part and a power supply to enable rotation of the rotor within the stator.

Figure 9:
FIG. 9 shows a side view of a first moving part in accordance with a preferred embodiment of the invention having a first, second and third screw thread, wherein the direction of rotation of the first (lower) and second (lower) screw threads are opposite to the direction of rotation of the third (upper) screw thread, and wherein the lower or tissue contact terminal region of the elongate shaft is free of any attached or associated screw threads.
Figure 10:
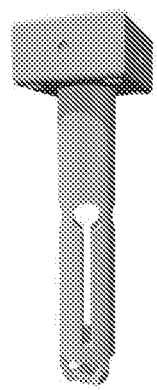
FIG. 10 shows an upright side view of a casing that is adapted for use in combination with the first moving part shown in FIG. 9, wherein the lower or tissue contact end of the casing further comprises a bracket having an opening that is aligned with or concentric with the longitudinal axis of the elongate shaft and is configured to accommodate the terminal region of the elongate shaft.
Figure 11:
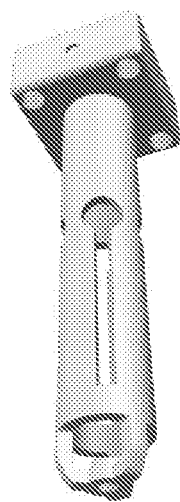
FIG. 11 a slanted side view of the casing shown in FIG. 10.

In FIG. 9 there is shown a further embodiment of the invention having the above described features, however in this embodiment the elongate shaft terminates in a thread-free region i.e. a central shaft that is without any thread. Moreover, the corresponding casing for this embodiment, shown in FIGS. 10 and 11, in addition to having the afore described features, also has an end bracket comprising a number of (in this embodiment three) interconnecting extensions with a central aperture. This aperture is aligned or concentric with the longitudinal axis of the elongate shaft and sized and shaped to accommodate same in a manner that provides clearance such that the elongate shaft can rotate with respect to said casing but is constrained in terms of the amount of lateral movement it can undergo. Whilst this feature is illustrated using an extending bracket, other conventional means may be employed to limit the degree of lateral movement of the rotating shaft with respect to the casing.

In use, the moving part is inserted into the casing and the rotor is activated to cause the shaft to turn. When in contact with a tissue sample, optionally suspended in buffer solution, this rotary motion disrupts the tissue and fragments/components thereof travel along the first/second screw thread(s) towards the expanded parts of the aperture from which they are discharged. The presence of an upper, oppositely wound, return thread ensures disrupted tissue does not travel above the exit aperture(s). Typically, the rotation speed(s) of said device ranges from 100-10,000 revolutions per minute. Moreover, the duration(s) of rotation (s) ranges from 10 seconds-10 minutes.

EXAMPLE 1

Use of the device to obtain stem cells from adipose tissue will now be described by way of example only.

Use of Device/Agitator for Adipose Tissue Dissociation
1. The casing/stator and the rotor/shaft within are placed in a vessel containing adipose tissue to be dissociated.
   a. The device/agitator mechanically dissociates the adipose tissue so that the stromal vascular fraction (SVF) comprising live, intact cells can be obtained.

Description of Fluid and Additives
1. Fluids used are biocompatible fluids including, but not limited to, normal saline, Hank's balanced salt solutions with or without calcium and magnesium, phosphate buffered salt solution with or without calcium and magnesium, Ringer's solution, lactated Ringer's solution, or Hartmann's solution.
   a. The fluid is added to the vessel in which the adipose tissue will be dissociated.
   b. The volume of fluid added is 10%-200% of the adipose tissue volume to be dissociated in the vessel.
2. The fluid may contain additives that are biocompatible/clinically approved excipients/reagents including, but not limited to, polyethylene glycol, polyvinyl alcohol, sucrose, glucose, albumin, amino acid, pyruvate, alone or in combination.
3. The fluid supports the viability of mammalian cells.
4. The additives aid to increase the number of live, intact stromal vascular fraction cells obtained, and/or the growth of these cells when the cells are cultured.

Description of Adipose Tissue and Adipose Tissue Storage
Adipose tissue is obtained in the following forms, and may be stored prior to dissociation.
1. As lipoaspirate or finely minced pieces.
2. The adipose tissue may be stored for 0 hours-72 hours before dissociation.
   a. Storage temperature ranges from 4° C.-18° C.
   b. Storage of adipose tissue may be with or without the fluids, and with or without the additives as described above.

Description of Dissociation Process
1. If stored, and if solid in appearance, the adipose tissue is thawed before dissociation, at room temperature or at 37° C. or until the adipose tissue regains a semi-solid appearance.

2. The thawed adipose tissue is placed in a vessel for dissociation.

3. The fluid, with or without the additives, is added to the thawed adipose tissue in the vessel.

a. The volume of fluid added is 10%-200% of the adipose tissue volume in the vessel.

4. The casing/stator and shaft/rotor is placed within the vessel containing the adipose tissue and fluid.

5. The tissue is dissociated by rotation of the rotor with or without rotating the stator.

a. The rotational speed(s) ranges from 100-10,000 revolutions per minute.

b. The duration(s) of rotation(s) ranges from 10 seconds-10 minutes.

Description of SVF Separation, Cryopreservation, and Cell Culture

After dissociation as described above, the SVF is separated from the adipocytes and oil by performing the following sequential steps.

1. The dissociated adipose tissue is centrifuged between 50-1000 times (50×-1000×) relative centrifugal force (RCF) to separate the dissociated adipose tissue into an oil and adipose tissue layer, and an aqueous layer containing the SVF.

a. The SVF may or may not be in the form of a cell pellet in the aqueous layer.

2. The oil and adipose tissue layers are separated from the aqueous layer and SVF.

3. If the SVF is in the form of a cell pellet, it is gently re-suspended in the aqueous layer to obtain a cell suspension.

4. The cell suspension is filtered through a filter that has pore sizes between 40-250 µm.

5. The filtered cell suspension is centrifuged between 50×-1000× RCF to obtain the SVF as a cell pellet.

6. Most of the fluid is removed, leaving only the SVF pellet and a small volume of the fluid.

a. The bottom of the fluid meniscus should be as close to, and less than 5 mm, from the top of the cell pellet.

7. The SVF is re-suspended in the remaining fluid by gentle shaking or tapping to obtain a concentrated cell suspension.

8. This step and procedures contained therein is optional and may be skipped.

i. Substantial red blood cells (RBCs) can be optionally removed by adding a RBC Lysis solution at 0.5 ml to 10 ml per SVF amount from 100 cc of adipose tissue.

ii. A volume of biocompatible fluid that is 1 to 10 times the volume of RBC Lysis solution is added, within 10 seconds to 60 seconds of adding RBC Lysis solution.

iii. The cell suspension is centrifuged from between 50×-1000× RCF to obtain the SVF as a cell pellet.

iv. As in Step 6, most of the fluid is removed, leaving only the SVF pellet and a small volume of the fluid.

v. The SVF is re-suspended in the remaining fluid by gentle shaking.

9. To culture the SVF, culture medium (e.g. DMEM containing 15% FBS, 1× NEAA, 5 ng/ml basic FGF, and 100 U/ml penicillin/streptomycin, or appropriate commercial media) is added to the concentrated cell suspension. The viable cells may be counted with a hemocytometer or automated cell counter prior to plating.

a. The cells are added into appropriate vessels and incubated in a standard 37° C., 5% CO2 humidified incubator.

b. The next day, the culture medium is removed and the adherent cells are gently washed with buffer (e.g. HBSS), and cultured with fresh culture medium.

c. Culture medium is changed as appropriate, and cell growth and morphology is observed under a microscope.

10. To cryopreserve the SVF, the viable cells may first be counted with a hemocytometer or automated cell counter prior to adding cryopreservation medium (e.g. DMEM containing 50% FBS and 10% DMSO, or appropriate commercial cryopreservant) to the concentrated cell suspension. Cryopreservation medium is added to obtain cells at a desired cell density for freezing (e.g. $1\text{-}2\times10^6$/ml) and the cells are gently re-suspended.

a. The cell suspension is aliquoted into appropriate vessels (e.g. 1 ml cryotube) and frozen at −80° C. under controlled-rate freezing.

b. After controlled-rate freezing, the vessels may be transferred to liquid nitrogen for long-term storage.

11. For clinical applications, the viable cells may first be counted with a haemocytometer or automated cell counter. After counting, the cell suspension is diluted with an appropriate clinical fluid to the desired cell concentration.

The invention claimed is:

1. A device for use in disrupting tissue, comprising:
a first moving part in the form of an elongate shaft having attached thereto or associated therewith at least two continuous or discontinuous screw threads;
a second non-moving part in the form of a casing adapted to fit over said elongate shaft and having at least one elongate aperture aligned with the longitudinal axis of said elongate shaft and being wider at an end remote from a tissue contact end, and
at least one screw thread of the at least two continuous or discontinuous screw threads is on the lower part or half of said elongate shaft, thereby forming lower threads, and at least one screw thread of the at least two continuous or discontinuous screw threads is on the upper part or half of said elongate shaft, thereby forming upper threads, and the direction of rotation of the upper threads is the opposite to the lower threads, wherein the upper threads ensure disrupted tissues do not travel along the entire length of said elongate shaft but rather is directed to exit where the lower threads end.

2. The device according to claim 1 wherein said moving part comprises a motor and a rotor.

3. The device according to claim 1, wherein said moving part comprises a handle or mounting via which the device can be held whilst in operation.

4. The device according to claim 1, wherein said at least two continuous or discontinuous screw threads are continuous.

5. The device according to claim 1, wherein said at least two continuous or discontinuous screw threads are discontinuous.

6. The device according to claim 1, wherein the angular arrangement of the at least two continuous or discontinuous screw threads is from 20°-88°, as measured from a horizontal plane.

7. The device according to claim 1, wherein the depth of the at least two continuous or discontinuous screw threads is less than 40% of the diameter of the casing.

8. The device according to claim 1, wherein said at least one elongate aperture comprises a plurality of elongate apertures.

9. The device according to claim 8 wherein there are between 2-12 elongate apertures per casing circumference.

10. The device according to claim 8, wherein there are 4 elongate apertures per 4.5 cm of casing.

11. The device according to claim 8, wherein said plurality of elongate apertures are evenly spaced about said casing.

12. The device according to claim 1, wherein said at least one elongate aperture comprises a slit at an end remote from said tissue contact end of said device.

13. The device according to claim 12, wherein said expanded part of said at least one elongate aperture forms at least a partial circular shape.

14. The device according to claim 12, wherein the expanded part of said at least one elongate aperture is aligned with the upper end of the lower threads or aligned with a junction between said lower and upper threads.

15. The device according to claim 1, wherein said at least one elongate aperture comprises a discontinuous slit at said end remote from said tissue contact end.

16. The device according to claim 1, wherein
a lower or tissue contact terminal region of the elongate shaft is free of any attached or associated screw thread(s), and
a lower or tissue contact end of the shaft or casing further comprises a constraining member such that, in use, the elongate shaft is free to rotate but is laterally restrained.

17. The device according to claim 1, wherein the angular arrangement of the at least two continuous or discontinuous screw threads is from 40°-80°, as measured from a horizontal plane.

18. The device according to claim 1, wherein the angular arrangement of the at least two continuous or discontinuous screw threads is from 40°-50°, as measured from a horizontal plane.

19. The device according to claim 1, wherein the depth of the at least two continuous or discontinuous screw threads is less than 30% of the diameter of the casing.

20. A method for disrupting tissue, comprising:
contacting the device according to claim 1, with a tissue sample whose component parts are to be mechanically separated; and
activating the elongate shaft, thereby disrupting the tissue sample.

21. The method of claim 20, wherein said tissue is suspended in a biocompatible fluid with or without additives.

22. The method of claim 20, wherein said device rotates at a speed(s) within the range of 100-10,000 revolutions per minute.

23. The method according to claim 20, wherein the duration of rotation ranges from 10 seconds-10 minutes.

24. The method of claim 21, wherein the biocompatible fluid comprises polyethylene glycol, polyvinyl alcohol, sucrose, albumin, amino acid, pyruvate, or combinations thereof.

* * * * *